(12) United States Patent
Drake

(10) Patent No.: US 8,844,989 B2
(45) Date of Patent: Sep. 30, 2014

(54) CONTACT LENS INSERTION AND REMOVAL DEVICE

(71) Applicant: Rita Drake, Fallbrook, CA (US)

(72) Inventor: Rita Drake, Fallbrook, CA (US)

( * ) Notice: Subject to any disclaimer, the term of this patent is extended or adjusted under 35 U.S.C. 154(b) by 0 days.

(21) Appl. No.: 13/894,316

(22) Filed: May 14, 2013

(65) Prior Publication Data

US 2013/0300140 A1    Nov. 14, 2013

Related U.S. Application Data

(60) Provisional application No. 61/646,659, filed on May 14, 2012.

(51) Int. Cl.
*A61F 9/00*    (2006.01)

(52) U.S. Cl.
CPC .................................. *A61F 9/0061* (2013.01)
USPC .......................................................... 294/1.2

(58) Field of Classification Search
USPC .......... 294/1.2, 183, 185, 210, 2, 24; 606/107
See application file for complete search history.

(56) References Cited

U.S. PATENT DOCUMENTS

| | | | | |
|---|---|---|---|---|
| 3,031,918 | A * | 5/1962 | Moyers | 294/1.2 |
| 4,126,345 | A * | 11/1978 | List | 294/1.2 |
| 4,387,921 | A * | 6/1983 | Licata | 294/1.2 |
| 4,512,602 | A * | 4/1985 | England | 294/1.2 |
| 4,753,470 | A * | 6/1988 | Menard | 294/1.2 |
| 7,347,466 | B1 * | 3/2008 | Feldman | 294/1.2 |

* cited by examiner

*Primary Examiner* — Dean Kramer
(74) *Attorney, Agent, or Firm* — Donn K. Harms

(57) ABSTRACT

A contact lens insertion and removal device having an elongated member cup shaped component or adjacent to a first end of the member and a resilient tip at or adjacent to a second end of the member. The resilient tip is employable by a user for contact lens insertion into their eye, while the cup shaped component may be employed for removal of a contact adhered to the eye.

6 Claims, 1 Drawing Sheet

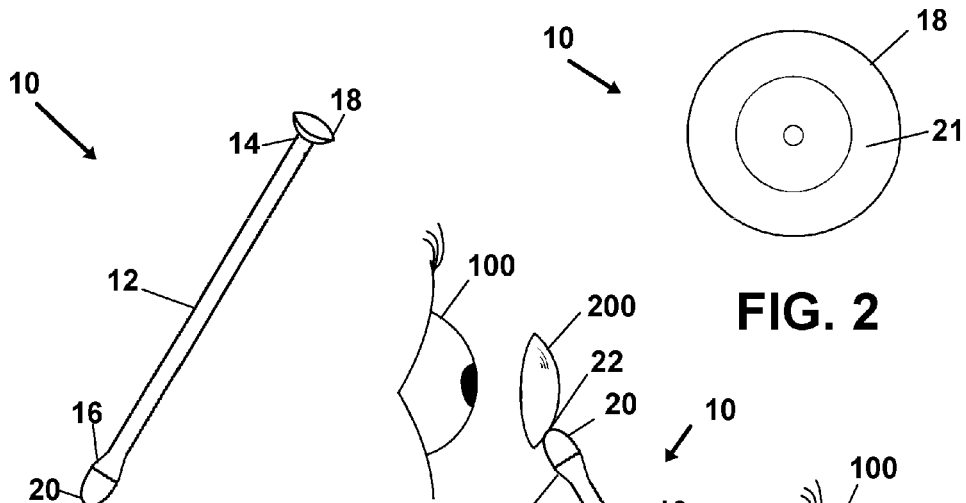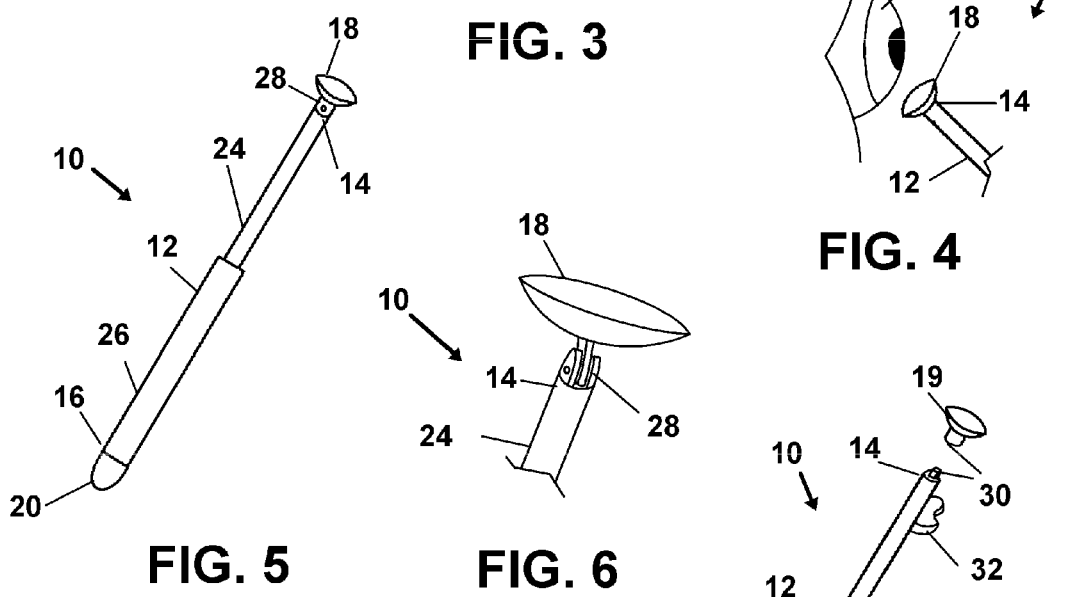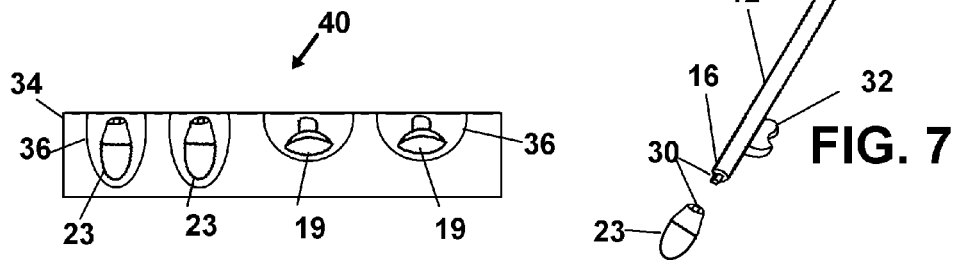

CONTACT LENS INSERTION AND REMOVAL DEVICE

This application claims priority to U.S. Provisional Application No. 61/646,659 filed on May 14, 2012, which is included herein in its entirety.

BACKGROUND OF THE INVENTION

1. Field of the Invention

The present invention relates to contact lenses. More particularly, the disclosed device relates to a contact lens insertion and removal device configured for employment using the hand of a user to more easily and sanitarily manipulate and insert contact lenses using an elongated member having an insertion component on a first end and a lens capturing component for removal thereof from the eye on a second end, opposite the first end.

2. Prior Art

The use of contact lenses has become more popular in recent years due to improvements in lens technology as well as cost providing easier accessibility to the average consumer. Soft contact lenses formed from synthetic hydrogels employed to correct vision, or for aesthetic purposes of eye color or both, are known to comfortably provide immediate vision improvement as they are easily wetted and most are formed of material allowing for sufficient oxygen permeability to allow oxygen to contact the eye.

The concave shape of modern soft lenses, when placed adjacent to and then in contact with the surface of a user's eye, tends to provide a suction adhesion to securely engage the lens to the surface of the eyeball. However, for users both new and seasoned with experience in the usage of such lenses, insertion and removal of the flexible and sometimes collapsed lens onto the surface of the eyeball can be time consuming, frustrating, and unpleasant, thereby rendering what appears at first to be a simple task, to one that is in fact difficult.

Further, more modernly, many soft contact lenses are formed for short time occupancy of the eye and are therefore formed of very thin material. While these thin contact lenses are generally more comfortable, they are considered "daily wear" wherein a user must consistently remove the lenses prior to sleeping, and the following day, must insert a new pair of lenses. Such lenses while comfortable, are not made to resist the perils of long term wear and are as such are generally more easily torn. Additionally unlike long term soft lenses or hard lenses, during insertion the curve of thin lenses tends to collapse when placed on the user's finger rendering the "cup" like engagement a much smaller target.

Conventionally, users will insert and remove the lens from each eye using one finger. In use, the soft lens is removed from a disposable package and positioned using a pair of fingers on one hand, which then places the lens with its exterior surface of wetted soft lens material atop one finger of the opposite hand. The moist nature of the lens tends to statically adhere it to the user's finger and allows them to manipulate the lens which has been removed from a package or carrying case, from a horizontal and supported position to a substantially vertical position with engaged by static adhesion or surface tension to a finger during insertion.

In a conventional removal from the eye, the user will often pinch or otherwise flex the lens between two opposing fingers, to break the surface tension and suction adhering the contacting surface of the curved lense, with the curved surface of the user's eyeball. Once so pinched, the user peals the lens off their eye. This removal effort requires deliberate movements and a keen sense of spatial relationships. Further it requires short fingernails and a bit of dexterity that is learned over time by most who can.

For insertion, it is important for the user to maintain a minimum contact surface area of the exterior of the contact lens, in a communication with a portion of their finger. This contact surface must be large enough to insure the lens will stay engaged to the finger when held in a substantially vertical disposition, but small enough to ensure that the finger will properly disengage from the lens once inserted to contact the opposite curved surface with the eye. If the user's finger adheres substantially to the contact lens, when the user pulls their finger away from an attempted insertion, the lens may inadvertently be tugged off the surface of the eye when it overcomes the suction adhesion. This may not only provide discomfort to the user, but in the case where the user has had LASIK surgery resulting in corneal flaps, the flaps may be torn from their position. Further, if the lens is torn away, the attractive force from the eye tends to pull the lens from the finger, and frequently the contact lens will end up on the floor or in a sink where sterility is at best questionable and normally unsatisfactory to allow for a reinsertion of the dropped lens.

As can be imagined, this system of insertion and removal of contact lenses can be very discomforting to the average user, and may result in degraded eyesight should they lose a lens and lack a replacement, or can result in eye infection if they reuse a dropped lens. Further, the simple act of a user being required to contact their eye with their finger is typically considered unpleasant and actually causes many potential contact lens users to instead continue to wear eyeglasses. In addition, there is a great chance of cross contamination from germs or viruses such as Herpes on the user's finger even if washed or sanitized.

For some users, daily repetition of insertion and removal allows them to become accustomed to the process which may eventually not become as bothersome. However such long term users frequently become complacent about proper hand hygiene prior to insertion and removal. Additionally, for other individuals, the process remains an uneagerly anticipated nuisance. For these users, it is often the fact that they must insert their finger into their eye, which is unsanitary and uncomfortable which defers them from the task. As a result, prior art has provided many contact lens insertion and removal devices in order to decouple the act of employing ones own finger with the process.

U.S. Pat. No. 4,221,414 to Schrier teaches such a device employing a pair of bifurcated members employed for grasping the lens for assisted insertion and removal. However, the device to Schrier requires the user to carefully and deliberately manipulate the members once in contact with the lens, which may prove extremely difficult if the user is squeamish and unable to maintain a steady hand. Further, the members of Schrier are pointed angular tips, which most users would avoid using lest they be required to position pointed objects in their eyes.

U.S. Pat. No. 4,286,815 to Clark teaches a lens insertion and removal device comprising a suction cup member having a concave surface coupled with a vacuum source. The device to Clark is employed by contacting the cup to the lens, applying a vacuum to engage the lens thereon, and manipulating the lens for either insertion or removal. However, the suction cup and vacuum applied thereon may inadvertently impart a vacuum on the surface of the eye, and the problems associated with corneal flaps may be present. Further, providing a vacuum source or means can be quite cumbersome and may not be desirable for travel and other reasons. Even in the absence of the vacuum, the device is configured such that a lens may maintain static adhesion to the cup member which may prove difficult for transferring the lens from the cup to the surface of the eye for insertion.

U.S. Pat. No. 6,398,277 to McDonald teaches an insertion device having a suction cup member fluidly engaged to a syringe. In use the lens is engaged within the cup member and a depression of the barrel of the syringe forces a fluid out of the syringe to eject the lens from the cup. The device advantageously provides the user with a means to additionally eject the fluid, such as water or a saline solution, if such is available in a desired mode of sanitation or sterilization. However, the device to McDonald requires deliberate manipulation while at or near the users eye and is intended for employment by physicians to a patient. Further, McDonald does not easily necessitate removal of contact lenses and requires ongoing purchasing and use of sterile fluids to be used properly.

These and similar prior art devices for soft contact lense insertion simply fall short. As such, there is a continuing unmet need for a contact lens insertion and removal device which is user friendly, requires no purchase of expensive fluids, is easily manipulated and sterile, and ensures proper disengagement of the device from the lens during lens insertion.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The invention herein disclosed and described provides a solution to the shortcomings in prior art and achieves the above noted goals through the provision of a contact lens insertion and removal device including an elongated member providing a hand engageable handle having a first end and a second end. At the first end is positioned a contact lens removal component currently formed in the configuration of a suction cup component. The cup component may be in a fixed engagement to the handle, or in a particularly preferred mode of the device it may be rotationally engaged thereon. To provide novelty and function for the user untaught by prior art, the curvature of the suction imparting cup component of the present invention preferably comprises a concave surface area which has an area that is substantially less than the surface area of a conventional contact lens for which the device is employed to insert or remove from an eye.

Experimentation required forming the cup component in a number of different surface areas all of which did not necessarily work well to the task. However, it has been found in accordance with a first preferred mode of the invention, that the cup component surface area works best when formed in an area which is from 10%-75% of the surface area of a conventional contact lens which it is to be engaged temporarily. Most contact lenses in the United States fall in the range of diameters from 12 mm to 18 mm with 14 mm to 16 mm being a widespread choice. However, it is noted that percentages outside the above noted range which are suitable for the intended purpose may also be employed, and are anticipated.

By providing a contact surface area which is substantially less then that of the 13 mm to 18 mm diameter of the contact lens, the chance of improperly removing the contact lens in a pinching motion, or by suction which can result in corneal flap agitation or movement is greatly reduced. For example, the user may easily position the relatively smaller curved cup component of the device, adjacent the terminating edge or circumferential edge of the contact lens in a manner to gently peal the lens of the surface of the eye. This can be accomplished in replacement of the conventional mode where two fingers pinch the lens and then tug to break the adhesion of the contact lens with the eye surface, as is commonly associated with other devices employing formed cup components. Further, no skin contact and resulting communication of pathogens, germs or viruses such as Herpes occurs using the device eliminating a common problem when lenses are inserted using a finger.

At the second end of the elongated member is positioned a lens insertion component providing means for lens insertion to the eye. In accordance with at least one preferred mode, the lens insertion component includes a soft rubber-like tip component engaged on a first side surface at or adjacent to the elongated member at a first end, and extending to a substantially rounded distal end. In use, the soft tip forms a means for surface adhesion of the soft plastic or soft tip to a wetted surface of a contact lens, and provides an easy dismount once so engaged. It has been found that minimizing the surface area of the soft tip, with the exterior surface of the contact lens to adequately engage the contact lens for manipulation from a horizontal position from a carrying case to a maintained vertical position adjacent to the eyeball, works best.

Further this minimized contact surface area additionally allows the device to properly disengaged once the lens has become engaged to the surface of the eyeball, to again minimize the chance of damage to the cornea, or dismounting of the lens which may fall to an unsanitary landing. The contact surface area of the tip is preferably equal to or less than 10%-20% of the surface area of a conventional contact lens which in the USA is conventionally 13 mm to 18 mm. As a consequence an contact surface on the tip, which is curved to form a generally circular area of contact between 1.3 mm to 2.6 mm is preferred.

In yet another particularly preferred mode, the device is providable to the user in a kit comprising a plurality of removably engageable suction imparting cup components and a plurality of plastic, polymer, or soft tip components. The suction imparting cup component and soft tip component may removably engage to the respective ends of the elongated member via snap fits or other means for removable engagement. The removably engageable components can be manufactured as disposable components for sanitation and convenience purposes.

In all preferred modes, the elongated member preferably includes an elevation component providing means for maintaining one or both of the ends elevated off a support surface when not in use, or when the device is sitting with a contact lens engaged and ready to insert. This elevation component can include one or a plurality of leg portions which act to prop or otherwise raise the ends off a support surface when the device is rested on a counter top or on a shelf surface for storage. The resulting spacing from the elevation will reduce the change of cross contamination from a support surface to the ends of the device. Other preferred means may include a slidable collar.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

It is an object of the invention to provide a contact lens insertion and removal device which is user friendly and sanitary.

It is an object of the invention to provide a lens removal means comprising a cup component having a contact surface area which is 10%-75% of the surface area of a conventional contact lens.

It is another object of the invention to provide a lens insertion means comprising a soft, rounded, soft tip having a contact surface area which is 10%-20% of the surface area of a conventional contact lens.

It is yet another object of the invention to provide a lens insertion and removal device which does not require insertion or removal of the contact lens in a manner which can dismount or agitate corneal flaps present on the surface of the eyeball.

It is still another object of the invention to provide a kit of removably engageable and disposable cup components and resilient plastic or soft tip component components.

Further objects of the invention will be brought out in the following part of the specification, wherein detailed description is for the purpose of fully disclosing the invention without placing limitations thereon.

BRIEF DESCRIPTION OF DRAWING FIGURES

The accompanying drawings, which are incorporated herein and form a part of the specification, illustrate some, but not the only or exclusive, examples of embodiments and/or features. It is intended that the embodiments and figures disclosed herein are to be considered illustrative rather than limiting. In the drawings:

FIG. 1 shows a view of a first preferred mode of the device comprised of an elongated member having a suction imparting cup component disposed at a first end and a rounded soft or rubber-like tip component disposed at a second end opposite the first end.

FIG. 2 shows an end view of the device of FIG. 1 showing the contact surface area of the cup component.

FIG. 3 shows a view of the device in the as used mode for inserting a contact lens onto the surface of a user's eyeball employing the soft tip component.

FIG. 4 shows a view of the device in another as used mode for removing a contact lens employing the suction imparting cup component.

FIG. 5 shows a view of another particularly preferred mode of the device comprised of a telescoping elongated member and having a rotationally engaged suction imparting cup component.

FIG. 6 shows a detailed view of the means for rotational engagement of the suction imparting cup component to the elongated member.

FIG. 7 depicts yet another particularly preferred mode of the device comprised of removably engageable suction imparting cups and soft tip components.

FIG. 8 shows a particularly preferred kit which is providable to the user comprising a plurality of removably engageable suction cup and soft tip components.

DETAILED DESCRIPTION OF THE PREFERRED EMBODIMENTS OF THE INVENTION

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

Now referring to drawings in FIGS. 1-8, wherein similar components are identified by like reference numerals, there is seen in FIG. 1 a view of a first particularly preferred mode of the contact lens insertion and removal device 10. In the current preferred mode the device 10 is comprised of an elongated member 12 having a first end 14 and a second end 16 which is configured for engagement between two fingers of a user's hand. A substantially concave suction imparting cup component 18 is engaged at or near the first end 14 and provides means for engagement to an inserted lens in the eye of the user for a lens removal.

A soft tip component 20 is engaged at or near the second end 16 of the elongated member 12 and provides means for temporary frictional or surface tensioned engagement of a contact lens thereto for a lens insertion. The soft tip component 20 preferably has a substantially rounded or curved distal end sized to make appropriate contact with the contact lens, and maintain a frictional or surface tensioned engagement from a horizontal positioning of the contact lens to a vertical positioning thereof. The various components of the device 10 disclosed herein can be formed of conventional materials such as soft or rigid synthetic plastics however can be formed of any material suitable for the purposes set forth in this disclosure.

It is noted and anticipated that although the device 10 is shown in its most simple form, various components and aspects of the device may be differently shaped or slightly modified when forming the invention herein. As such those skilled in the art will appreciate the descriptions and depictions set forth in this disclosure or merely meant to portray examples of preferred modes within the overall scope and intent of the invention, and are not to be considered limiting in any manner.

In a current preferred mode of the device 10, the cup 18 component and soft tip component 20 may be formed as a unitary structure in combination with the elongated handle 12. In this mode, the device 10 may be formed by any conventional method known in the art such as injection molding or machining.

In another preferred mode, the elongated member 12, acting as a handle, is to be formed of a rigid plastic or metal, while the cup 18 component and tip 20 component are formed from soft plastic or rubber-like resilient material. In this mode the device 10 can be formed from a two or multi-shot injection molding process, or by providing means for engagement of the cup component 18 and tip component 20 to their respective ends of the member.

FIG. 2 shows an end view of the device 10 of FIG. 1 detailing the surface area 21 of the concave cup component 18. It is particularly preferred that the surface area 21 be in the range of 10%-75% of the surface area of a conventional contact lens which has a diameter range from substantially 13 mm to 18 mm. The diameter of the cup component 18 thus would range between 1.3 mm to 13.5 mm.

However, it is noted and anticipated that values outside the stated range which are suitable for the intended may also be employed. To be described in more detail later, by providing a contact surface area 21 which is substantially less than that of the area of the curved exterior surface of a conventional contact lens, opposite the surface contacting the eye, the contact lens can more easily be disengaged from the surface of eyeball without agitating or disturbing the cornea.

FIG. 3 shows a view of the device 10 in a first as-used mode for inserting a conventional contact lens 200 onto a contact engagement with the surface of an eyeball 100. As is conventionally known in the art, lenses 200 are maintained substantially moist or wetted, such that the soft tip component 20 can engage temporarily on the exterior surface of the contact lens 200 via static adhesion. This adhesion is sufficient to maintain the contact from a transition from a horizontal positioning of the contact lens 200 to a vertical positioning of the contact lens 200 during eye contact.

Further, the substantially rounded soft tip component 20 is curved to provide a contact surface 22 area which is preferably 10%-20% of the surface area of the exterior surface of the contact lens 200. A current preferred range of the area of contact of the soft tip component 20 is between 1.3 mm to 3.6 mm. Once the larger eye contacting surface of the lens 200 is engaged to the surface of the eye 100, the device 10 may effectively disengaged from the lens 200 as needed as the adhesion force to the eye exceeds that of the soft tip component 20 to the contact lens.

FIG. 4 depicts the removal of a contact lens 200 from the surface of an eyeball 100. As shown, the suction imparting cup component 18 having a contact surface area 21 substantially less then that of the surface area of the exterior surface of the contact lens 200 allows the user to engaged the cup 18 and remove the contact lens 200 in a manner that does not agitate or disturb the cornea or tear the contact lens.

For example the cup component 18 can be engaged to the contact lens adjacent to the terminating edge of the lens 200 such that the user can gently peel the lens off the surface of the eye without much needed force. Further, the substantially smaller cup 18 area gives the user more room for error for sufficiently engaging the lens 200, as opposed to prior art cups which are sized substantially similar to the size of the actual contact lens.

FIG. 5 shows another particularly preferred mode of the device 10 providing a telescopic elongated member 12 formed from a telescopic engagement of a first component 24 and a second component 26. In this mode of the device 10 the adjustable length of the member 12 allows the user to extend or retract the elongated member 12 to a desired length to better allow them to insert and remove a contact lens as needed. The elongated member 12 may include a locking means to allow the user to positionably lock the components 24, 26 to the desired length such as a twisting frictional engagement.

A first end 14 of the elongated member 12 formed on the first component 24 additionally includes means for a threaded rotational engagement of the cup component 18 thereon using mating threads in the cup component 18. In other modes the means for rotational engagement can be any means known in the art, for example a ball joint, or rotational joint providing a hinge 28. Using this rotational mount, the user may selectively position the angle of the cup 18 as needed for their individual hand and eye coordination and body configuration.

FIG. 6 shows a detailed view of the rotational engagement provided by the hinge 28 providing means for rotational engagement of the cup 18 to the end 14 of the first component 24. Ball joint frictionally positioned requiring user force to reposition could also be used.

FIG. 7 is a view of still yet another particularly preferred mode of the device 10 providing a removably engageable cup 19 and soft tip 23. The means for removable engagement can be any means known in the art, for example, snap fits 30. Or a frictional engagement of a cavity in the soft tip, over a member.

Further, the device 10 is shown having one or a plurality of projections 32 extending from the elongated member 12 to provide a means to maintain the ends 14, 16 a distance elevated above a support surface when the device 10 is not in use, or in-between uses on both eyes, to reduce the chance of cross contamination from contaminants on the support surface to the cup 18 (or 19) and soft tip 20 (or 23). Other means to raise the ends 14, 16 can include one or a plurality of slidable collars, or other means one skilled in the art may readily recognize, and are anticipated.

It is additionally noted that the provisions of the current mode of the invention may be employed in combination with any of the preferred modes of the invention and should not be considered limited.

FIG. 8 shows a view of a particularly preferred mode of the device 10 being a kit 40 comprised of a container 34 having a kit of a plurality of removably engageable tip and cup components 19, 23 engaged therein. As is shown, the components 19, 23 may be engaged within sealed sterile cavities 36. The kit 40 may be providable to the user with or without the elongated member 12, which may be sold separately.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A contact lens insertion and removal apparatus, comprising:
   an elongated member having a first end and second end;
   a cup shaped component;

means for engagement of a first surface of said cup shaped component at or adjacent to said first end of said member;

a resilient tip;

means for engagement of said resilient tip at or adjacent to said second end of said member;

said cup component having a second surface opposite said first surface defining a cup, said cup having an area defined by said second surface inside a circumferential perimeter edge of said cup component;

said circumferential perimeter edge sized smaller than a circumference of a contact lens for insertion into operative engagement with the eye of a user; and said tip having a curved contact surface area adapted for a contact adhesion with only a portion of one side surface of said contact lens, whereby said contact lens is engageable to said contact adhesion by said user for positioning in said operative engagement with said eye, and said contact lens is removable from said operative engagement by a suctional engagement of said cup component with a portion of one said side surface of said contact lens and a subsequent lifting of said contact lens from said eye;

said means for engagement of a first side of said cup shaped component at or adjacent to said first end of said member forming a removable engagement at or adjacent to said first end whereby said cup shaped member is removable and replaceable;

said means for engagement of said resilient tip at or adjacent to said second end of said member forming a removable engagement, whereby said resilient tip is removable and replaceable;

said resilient tip being one or a plurality of resilient tips provided in a kit of said resilient tips, each of said plurality of resilient tips positionable in a said removable engagement at or adjacent to said second end; and said cup shaped component being one or a plurality of cup shaped components provided in a kit of said cup shaped components, each of said plurality of cup shaped components positionable in a said removable engagement at or adjacent to said first end, whereby either or both of said cup shaped component and said resilient tip is removable and replaceable by said user.

2. The contact lens insertion and removal apparatus of claim 1, additionally including:

each of said plurality of cup shaped components having a different sized circumferential perimeter;

each of said plurality of resilient tips having a differently sized curved contact surface area; and said user chooses one said cup shaped component and one said resilient tip sized for operative engagement with a user's contact lens.

3. The contact lens insertion and removal apparatus of claim 2, additionally including:

said means for engagement of a first side of said cup shaped component at or adjacent to said first end of said member forming a rotational engagement of said cup at or adjacent to said first end; and said rotational engagement allowing for an adjustment of an angle of said cup shaped component relative to said elongated member.

4. The contact lens insertion and removal apparatus of claim 1, additionally including:

said means for engagement of a first side of said cup shaped component at or adjacent to said first end of said member forming a rotational engagement of said cup at or adjacent to said first end; and said rotational engagement allowing for an adjustment of an angle of said cup shaped component relative to said elongated member.

5. The contact lens insertion and removal apparatus of claim 4, additionally including:

an elevation component extending from said elongated member between said first end and said second end; and said elevation component maintaining said elongated member, and said cup shaped component and said resilient tip, spaced from a contact with a support surface on which said elevation component rests.

6. The contact lens insertion and removal apparatus of claim 1, additionally including:

an elevation component extending from said elongated member between said first end and said second end; and said elevation component maintaining said elongated member, and said cup shaped component and said resilient tip, spaced from a contact with a support surface on which said elevation component rests.

* * * * *